United States Patent [19]

Williams et al.

[11] Patent Number: 5,527,384
[45] Date of Patent: Jun. 18, 1996

[54] PRESERVATIVES FOR WOOD AND OTHER CELLULOSIC MATERIALS

[75] Inventors: Gareth Williams, Netherton; Judith A. Cornfield; Janet Brown, both of Castleford; Neil P. Ryan, South Elmsall, all of Great Britain

[73] Assignee: Hickson International, Plc, Castleford, England

[21] Appl. No.: 190,108

[22] PCT Filed: Aug. 3, 1992

[86] PCT No.: PCT/GB92/01427

§ 371 Date: Apr. 4, 1994

§ 102(e) Date: Apr. 4, 1994

[87] PCT Pub. No.: WO93/02557

PCT Pub. Date: Feb. 18, 1993

[30] Foreign Application Priority Data

Aug. 1, 1991 [GB] United Kingdom .................. 9116672
Jul. 6, 1992 [NZ] New Zealand .......................... 243460

[51] Int. Cl.$^6$ ................................................. A01N 43/653
[52] U.S. Cl. ........................ 106/18.32; 424/630; 424/638; 514/383; 514/491; 514/500
[58] Field of Search ........................ 106/18.32; 424/638, 424/630; 514/383, 491, 492, 500

[56] References Cited

U.S. PATENT DOCUMENTS

| | | | |
|---|---|---|---|
| 2,041,655 | 5/1936 | Gilbert | 424/604 |
| 3,976,594 | 8/1976 | Dahlgren | 252/400.2 |
| 4,143,153 | 3/1979 | Pommer et al. | 514/494 |
| 4,288,249 | 9/1981 | Amundsen et al. | 106/18.35 |
| 4,382,884 | 5/1983 | Rohringer et al. | 252/606 |
| 4,420,542 | 12/1983 | Sowers | 428/541 |
| 4,461,721 | 7/1984 | Goettsche et al. | 252/607 |
| 4,648,988 | 3/1987 | Van Dijck et al. | 252/602 |
| 4,652,580 | 3/1987 | Janssen et al. | 514/383 |
| 4,845,111 | 7/1989 | Brandes et al. | 514/383 |
| 4,845,112 | 7/1989 | Brandes et al. | 514/383 |
| 4,849,440 | 7/1989 | Brandes et al. | 514/383 |
| 4,886,825 | 12/1989 | Ruess et al. | 514/383 |
| 4,897,410 | 1/1990 | Brandes et al. | 514/383 |
| 4,902,704 | 2/1990 | Brandes et al. | 514/383 |
| 4,933,337 | 6/1990 | Brandes et al. | 514/383 |
| 4,933,358 | 6/1990 | Brandes et al. | 514/383 |
| 5,013,746 | 5/1991 | Van Gestel et al. | 514/383 |
| 5,013,748 | 5/1991 | Radtke et al. | 514/383 |
| 5,059,617 | 10/1991 | Brandes et al. | 514/383 |
| 5,078,912 | 1/1992 | Goettsche et al. | 252/400.53 |
| 5,082,855 | 1/1992 | Brandes et al. | 514/383 |
| 5,156,673 | 10/1992 | Metzner | 106/15.05 |
| 5,187,194 | 2/1993 | Goettsche et al. | 514/499 |
| 5,200,421 | 4/1993 | Ludwig et al. | 514/383 |
| 5,216,007 | 6/1993 | Miller et al. | 514/383 |
| 5,221,758 | 6/1993 | Maynard | 556/7 |
| 5,223,178 | 6/1993 | Leightley et al. | 252/380 |
| 5,223,524 | 6/1993 | Valcke | 514/383 |
| 5,230,892 | 7/1993 | Feyen et al. | 424/409 |
| 5,252,594 | 10/1993 | Shaber et al. | 514/383 |

FOREIGN PATENT DOCUMENTS

| | | |
|---|---|---|
| B1-35221/78 | 4/1978 | Australia . |
| 66642/86 | 12/1986 | Australia . |
| 70428/87 | 9/1987 | Australia . |
| 64786/90 | 4/1991 | Australia . |
| 15117/92 | 10/1992 | Australia . |
| 1185896 | 4/1985 | Canada . |
| 1284854 | 6/1987 | Canada . |
| 1249510 | 1/1989 | Canada . |
| 2028228 | 4/1991 | Canada . |
| 0089958 | 12/1985 | European Pat. Off. . |
| 102540 | 1/1986 | European Pat. Off. . |
| 252366 | 1/1988 | European Pat. Off. . |
| 315850 | 5/1989 | European Pat. Off. . |
| 447756 | 9/1991 | European Pat. Off. . |
| 448932 | 10/1991 | European Pat. Off. . |
| 453922 | 10/1991 | European Pat. Off. . |
| 2140051 | 8/1971 | Germany . |
| 3231347 | 3/1984 | Germany . |
| 2194752 | 3/1988 | United Kingdom . |
| WO85/00040 | 1/1985 | WIPO . |
| WO89/08395 | 9/1989 | WIPO . |
| WO91/11306 | 8/1991 | WIPO . |
| WO93/02557 | 8/1992 | WIPO . |

OTHER PUBLICATIONS

Goodwine, et al., "Suitability of Propiconazole as a New Generation Wood–Preserving Fungicide", American Wood Preservers' Association, pp. 206–214 (1990). No Month.

Page, R. G., Thomson, W. T., *The Insecticides, Herbicides, Fungicides Quick Guide,* (1985) p. 108. No Month.

Preservative Treatment for Sawn Tiber, Veneer and Plywood, Australian Standard as 1604–1980, p. 13. (No Month).

Valcke, A., "Suitability of Propiconazole (R 49362) as a New Generation Wood Preserving Fungicide," *20th Annual Meeting of International Research Group on Wood Preservation* Congress Centre, Lappeenranta, Finland, May 22–26, 1989.

Buschhaus, H., "Preventol A8–A Modern Wood Fungicide," *Eur. Polym. Paint Colour J.,* 182:4309, pp. 351–352. (Jun. 1992).

Culbreath, A. K., et al., "Use of a Resistant Peanut Cultivar with Copper Fungicides and Reduced Fungicide Applications for Control of Late Leaf Spot," *Crop Protection,* vol. 11, Aug. 1992, pp. 361–365.

Goodwine, W. R., "Suitability of Propiconazole as a New--Generation Wood–Preserving Fungicide," *Chemical Abstracts,* 114:242686t (1991) No Month.

Groth, D. E., et al., "Foliar Fungicides for Control of Rice Diseases in the United States," *Pest Management in Rice,* ed. Grayson, et al., published for the Society of Chemical Industry by Elsevier Applied Science. (No Date).

(List continued on next page.)

Primary Examiner—Anthony Green
Attorney, Agent, or Firm—Cheryl K. Zalesky; Kilpatrick & Cody

[57] ABSTRACT

The instant invention concerns a wood preservative composition comprising a synergistically effective amount of (a) a cuprammonium compound and (b) tebuconazole to preserve wood.

5 Claims, 4 Drawing Sheets

OTHER PUBLICATIONS

Gruening, R., et al., "Azaconazole–Based Compositions as Wood preservatives," *Chemical Abstracts* 112:2614h. (1990) No Month.

Leemput, L. V. et al., "Introductory Studies on the Environmental Fate of Azaconazole, a New Fungicide for Wood Preservation," *Chem. Prot. Environ. 1985*, Elsevier, pp. 163–182. No Month.

Metzner, W., "Azaconazole–Containing Wood Preservatives," *Chemical Abstracts* 110:90628c. (1989) No Month.

Valke, A. R., and Goodwine, W. R., *Azaconazole, A New Wood Preservative*, American Wood Preservers Association, 1985 No Month.

The Pesticide Manual, published by The British Crop Protection Council. (1987) No Month.

"Dictionary of Organic Comounds," 5th Ed., vol. 5, pp. 5388–5389, entries T–02376 and T–02377 (1983) No Month.

Grundlinger, R., et al., "Tebuconazole—A New Triazole Fungicide for Wood Preservation," *The International Research Group on Wood Preservation*, Paper prepared for the 21st Annual Meeting in Rotorua, New Zealand, May 13–18, 1990.

Wustenhofer, B., et al., "Tebuconazole, a New Wood–Preserving Fungicide," *The International Research Group on Wood Preservation*, paper prepared for the 21st Annual Meeting Rotorua, New Zealand, May 13–19, 1990.

Tamblyn, N., "Proceedings of the Tenth Forest Products Research Conference," (1961) Melbourne, pp. 86–107. No Month.

Thompson, E., et al., "The Chemistry of Wood Preservation," *Society of Chemistry* (1991) No Month.

The Australian Standard AS 1604–1980, p. 13 (1980) No Month.

Johnson and Thornton, "An Australian Test of Wood Preservatives II. The Condition after 25 Years' Exposure of Stakes Treated with Waterbone Preservatives," *Material and Organsimen* (1991), vol. 26, pp. 303–315 No Month.

Johnson, Thornton & Saunders, "An In–Ground Natural Durability Field Test of Australian Timbers and Exotic Reference Species III. Results after Approximately 15 Years' Exposure," *Material and Organismen*, vol. 21, pp. 251–264 (1986) No Month.

Greaves, et al., "Laboratory Tests on Light Organic Solvent Preservatives for use in Australia Part 4, Assessment of Several New Candidate Fungicides," *J. Inst. of Wood Science*, (1988) pp., 21–27, 103–107, 145–148 No Month.

Graves, H., "Wood Preservation in Australia," (1984), Appendix 1, pp. 54–55 No Month.

"Pesticide Index" (1988), p. 163 No Month.

Browning, "The Chemistry of Wood," (1975) p. 430 No Month.

Cotton and Wilkson, "Advanced Inorganic Chemistry," (1992) p. 756 No Month.

Wallis, A. F. A., "Wood Pulping with Mono—, Di— and Triethanolamine," *Appita*, vol. 31, No. 6, May, 1978.

Chin, et al., "Pigment Emulsified Creosote—An Alternative to High Tempature Creosote," *Proc. 21st Forest Products Conference*, Melbourne, Australia (1984) No Month.

Cookson and Greaves, "An Accelerated Field Simulator Trial of Metal Soaps," *Holzforschung*, (1991) vol. 45, pp. 19–22 No Month.

Chin, et al., "Recent Advances in Oil–Based Preservative Emulsions in Austrlia," i Proc. 22nd Forest Products Conference, Melbourne, Australia (Nov. 1986).

PRESERVATIVES FOR WOOD AND OTHER CELLULOSIC MATERIALS

This invention relates to preservatives for wood and other cellulosic materials.

The use of biocidal metal ions in wood preservation is well known. There are also many compounds containing a triazole group which are known to possess biocidal properties.

According to the present invention there are provided preservative compositions comprising a biocidal metal compound and a fungicidal compound containing a triazole group wherein the weight ratio of metal atom: fungicidal compound containing the triazole group is at least 1:2.5; with the specific exceptions of (i) composition (a) which contains 1.320% by weight of sodium nitrite, 1.190% by weight of copper sulphate. $5H_2O$, 0.400% by weight of boric acid, 0.625% by weight of sodium heptonate, 0.390% by weight of sodium hydroxide, 0.012% by weight of tebuconazole, 0.391% by weight of surfactant blend in xylene and 95.762% by weight of water and (ii) composition (b) which contains 0.00025% by weight of a compound of formula:

0.025% by weight of a compound of formula 2.525% by weight of dimethylformamide, 0.006313% by weight of alkylarylpolyglycolether the remainder being water.

We have found that compositions according to the invention possess advantageous properties: in particular, it has been found that the metal compound and the fungicidal compound containing the triazole group (hereinafter "the triazole compound") exhibit synergistic fungicidal activity.

It will be understood that the metal compound may be present in a form such that metal ions are free in solution or may form part of a complex. Similarly, the triazole compound may be free in solution or may be present in the form of a salt or a complex. For example, the triazole compound could be present in the form of a complex with part of the biocidal metal ion.

The compositions according to the invention may be used to treat substrates such as wood or other cellulosic materials (such as cotton, hessian, rope and cordage). For convenience, the invention will be described hereinafter with reference to the treatment of wood but it will be appreciated that the other materials may be treated analogously.

The metal compound may be a compound of any biocidally active metal including copper, aluminum, manganese, iron, cobalt, nickel, zinc, silver, cadmium, tin, antimony, mercury, lead and bismuth. These may be either used alone or in mixtures. The preferred metals are copper and zinc used alone, in combination with each other or with one or more of the metals listed previously. The most preferred metal is copper, particularly Cu (II) ion.

The triazole compound may be any compound which contains a triazole group and which possesses biocidal activity. Preferably the triazole compound contains the triazole group.

Advantageously, the triazole compound is selected from compounds of formula (A):

wherein $R_1$ represents a branched or straight chain $C_{1-5}$ alkyl group (e.g. t-butyl) and $R_2$ represents a phenyl group optionally substituted by one or more substituents selected from halogen (e.g. chlorine, fluorine or bromine) atoms or $C_{1-3}$ alkyl (e.g. methyl), $C_{1-3}$ alkoxy (e.g. methoxy) phenyl or nitro groups.

A particularly preferred compound of formula (A) is tebuconazole:
alpha-[2-(4-chlorophenyl)ethyl]-alpha(1,1-dimethylethyl)-1H-1,2,4-triazole-1-ethanol.

Alternatively, the triazole compound is advantageously selected from compounds of formula (B):

wherein $R_3$ is as defined for $R_2$ above and $R_4$ represents a hydrogen atom or a branched or straight chain $C_{1-5}$ alkyl group (e.g. n-propyl).

Particularly preferred compounds of formula (B) are: propiconazole (1-[[2-(2,4-dichlorophenyl)-4-propyl- 1,3-dioxolan-2-yl]methyl]-1H-1,2,4-triazole) and azaconazole (1-[[2,4-dichlorophenyl)-1,3-dioxolan-2-yl]methyl]-1H-1,2,4-triazole).

Hexaconazole and difenaconazole are examples of further triazole compounds which may be used in the compositions of the invention.

Compositions may contain more than one triazole compound for example, they may contain tebuconazole and propiconazole, or a mixture of tebuconazole, propiconazole and azaconazole.

We have found that the biocidal metal may advantageously be incorporated into the composition in the form of inorganic salts of the metal ion e.g. in the form of the metal carbonate, sulphate, chloride, hydroxide, borate, fluoride or oxide. Alternatively the metal may be used in the form of the metal salt of simple organic compound e.g. in the form of a salt of a carboxylic acid such as a metal acetate. Thus, it has been found that the biocidal triazole compounds exhibit synergistic properties when the metal ion is present in the form of such simple salts, and it is not necessary to add the metal ion in the form of a salt of, or complex with, a larger more complex organic compound which itself possesses biocidal properties.

The optimum weight ratio of metal ion to triazole compound varies depending on the particular material or product to which the composition is applied and the type of organism against which protection is required. Preferably the ratio by weight of metal to triazole compound is less than 1000:1, e.g. no greater than 750:1. More preferably, the weight ratio of metal: triazole compound should be between 750:1 and 1:1, particularly preferably between 500:1 and 2:1; most preferably the said ratio is between 50:1 and 5:1, especially about 25:1.

The concentration required for preservative treatment depends on the ratio of metal to triazole compound selected, the metal chosen, the method of treatment employed, the timber species, the level of protection required and the nature and quantity of any other biocides present. The levels necessary can be determined readily by one skilled in the art. In general, the level of metal required will be in the range 0.01–5% and the level of triazole will be in the range 25 ppm to 1.0%. The preferred range for waterborne treatments is to have a metal concentration of 0.1–5% and a triazole level of 50 ppm to 5000 ppm.

Compositions in accordance with the invention may if desired additionally contain nitrite ion. Alternatively, there can be advantages associated with the omission of nitrite ion from the compositions for example, by leaving out nitrite ion the formation of certain noxious gases is prevented.

The compositions of the present invention advantageously contain a biocidally active quaternary ammonium compound or tertiary amine salt. These compounds aid in the formation of emulsions of triazole compounds in aqueous solutions of biocidal metal ion. Compositions containing quaternary ammonium compounds or tertiary amine salts can form micro-emulsions which are particularly useful in the treatment of timber. In addition, the presence of these compounds may mean that additional organic solvents are not necessary to solubilise the triazole compound. Furthermore, the quaternary ammonium compounds and tertiary amine salts are themselves biocidal and so they enhance the overall biocidal activity of the composition. These compounds also improve penetration of the biocidal metal ion and triazole compound into the timber.

The composition in accordance with the invention may contain water as solvent, or an organic solvent or a mixture of solvents. Formulations can be prepared as concentrates intended to be diluted at the treatment facility, or the formulations can be prepared in the form of dilute treatment solutions. Optionally, separate solutions of biocidal metal ion and triazole compound can be provided e.g. in the form of two concentrates intended to be mixed before or after dilution.

Suitable formulations may be prepared, for example, by preparing aqueous solutions of metal ion complexes and subsequently adding an emulsified formulation of the triazole compound. Suitable complexing agents for the metal ion would be for example, polyphosphoric acids such as tripolyphosphoric acid, ammonia, water soluble amines and alkanolamines capable of complexing with biocidal cations; aminocarboxylic acids such as glycine, glutamic acid, ethylenediaminetetra-acetic acid, hydroxyethyldiamine triacetic acid, nitrilotriacetic acid and N-dihydroxy ethylglycine; polymeric compounds which contain groups capable of complexing with metallic cations such as polyacrylic acids; hydroxycarboxylic acids such as tartaric acid, citric acid, malic acid, lactic acid, hydroxybutyric acid, glycollic acid, gluconic acid and glucoheptonic acid; phosphonic acids such as nitrilotrimethylene phosphonic acid, ethylenediaminetetra (methylene phosphonic acid), hydroxyethylidene diphosphonic acid. Where the complexing agents are acidic in nature they may be employed either as free acids or as their alkali metal or ammonium salts. These complexing agents may be used either alone or in combination with each other. Suitable surfactants for triazole compounds include, for example, cationic, nonionic, anionic or amphoteric surfactants.

Suitable formulations can also be prepared, for example, by adding an emulsified formulation of the triazole compound to an aqueous solution of a metal salt, such as copper sulphate or zinc acetate. At high ratios of metal ion to azole, the solubility of the azole may be sufficient to disperse the azole in the formulation using a suitable co-solvent.

Alternatively, formulations can be prepared employing only organic solvents. To prepare such formulations, a biocidal metal salt of a carboxylic acid (e.g. decanoic or octanoic acid) is prepared and dissolved in a suitable organic solvent to form a concentrate. The triazole compound can then be added directly to the concentrate or to a solution diluted with a suitable solvent such as an ester, alcohol, ester alcohol, aliphatic or aromatic hydrocarbon, glycol ether, glycol or ketone.

Concentrated formulations containing organic solvents can optionally be mixed with water to form an emulsion which can be stabilized with surfactants if necessary.

Compositions in accordance with the invention can optionally contain other additives conventionally employed in timber preservation such as water repellents, color additives, viscosity modifiers or corrosion inhibitors.

The compositions of the invention may contain other organic compounds including fungicides, insecticides and bacteriocides. Such organic compounds include carboxylic acids such as naphthenic acids and branched aliphatic acids and their metal salts such as copper and zinc naphthenate, phenols and substituted phenols such as orthophenyl phenol and its alkali metal or ammonia salts; polyhalogenated phenols such as pentachlorophenol or tribromophenol and their alkali metal or ammonia salts; quaternary ammonium salts and tertiary amine salts such as didecyl dimethyl ammonium chloride, octyl decyl dimethyl ammonium chloride, dodecyl dimethyl benzyl ammonium chloride, dodecyl benzyl trimethyl ammonium chloride, dodecyl dimethyl amine acetate, dodecyl dimethyl amine lactate, dodecyl dimethyl amine salicylate, didodecyl methyl amine chloride; isothiazolone derivatives such as 4,5-dichloro-2-(n-octyl)-4-isothiazolin-3-one or 2-methyl-4-isothiazolin- 3-one, 2n-octyl-4-isothiazolin-3-one and mixtures of those and other related compounds; sulphamide derivatives such as N,N-dimethyl-N-phenyl-(N-fluorodichloro-methylthio)-sulphonamide, N,N-dimethyl-N-tolyl-N-(dichlorofluoro-methylthio)-sulphamide; azoles such as imidazole; MBT (methylene-bis thiocyanate); IPBC (3-iodo-2-propanyl-butyl-carbamate); carbendazim and chlorothalonil; N-nitrosophenylhydroxylamine and N-nitroso cyclohexyl hydroxylamine, either as their metal salts or as metal chelates; pyrethroid type insecticides selected from the group consisting of cyano-(4-fluoro-3-phenoxyphenyl)-methyl- 3-(2, 2-dichloroethenyl)-2,2-dimethyl-cyclopropanecarboxylate, (3-phenoxyphenyl)-methyl- 3-(2,2-dichloroethyenyl)-2,2-dimethylcyclopropanecarboxylate, cyano-(3-phenoxyphenyl)-methyl- 2-(4-chlorophenyl)-3-methylbutyrate, and mixtures thereof; organo-phosphorous, carbamate and organochlorine insecticides such as lindane.

Other biocidally active elements may also be present such as boron, in any form, for example boric acid, boron or boron esters and also fluorides and silicafluorides.

Particularly preferred compositions in accordance with the invention comprise copper (II) ion, a triazole compound which is tebuconazole or propiconazole, and an alkanolamine, as well as borate ion and/or a quaternary ammonium compound or a mixture of quaternary ammonium compounds.

According to a further aspect of the invention there is provided a method of treating a substrate of the type hereinbefore defined which comprises applying to the substrate a composition as defined above. Also within the scope of the invention is a method of treating a substrate of the type hereinbefore defined which comprises applying to the substrate composition (b) as defined above.

The skilled man will be well acquainted with the various methods of treating the substrates with aqueous solutions. For example, the compositions according to the invention may be applied to wood by dipping, spraying, deluging, brushing and by vacuum and/or pressure impregnation. Other types of substrate may be treated by analogous methods.

The following non-limiting Examples further illustrate the invention.

EXAMPLES

The compositions of Examples 1 to 3 may be prepared by adding an emulsified formulation of the triazole compound to an aqueous solution of a metal complex.

| | % w/w |
|---|---|
| Example 1 A concentrate formulation; metal to azole ratio 25:1 | |
| Basic copper carbonate | 10.9 |
| Monoethanolamine | 23.1 |
| Boric acid | 16.9 |
| Tebuconazole | 0.24 |
| Xylene | 3.76 |
| Process oil | 4.00 |
| Anionic/non-ionic emulsifier | 1.00 |
| Water | 40.10 |
| Example 2 A ready to use solution; metal to azole ratio 10:1 | |
| Copper sulphate pentahydrate | 1.18 |
| Lactic acid | 2.13 |
| Sodium nitrite | 1.31 |
| Boric acid | 0.79 |
| Ammonium hydroxide | 0.57 |
| Tebuconazole | 0.03 |
| Cypermethrin | 0.05 |
| Methyl dioxitol | 0.64 |
| Anionic/non-ionic emulsifier | 0.08 |
| Water | 93.22 |
| Example 3 A ready to use solution; metal to azole ratio 5:1 | |
| Basic copper carbonate | 0.55 |
| Ammonium hydroxide | 0.65 |
| Ammonium bicarbonate | 0.33 |
| Propiconazole | 0.06 |
| Naphthenic acid | 0.15 |
| Anionic/non-ionic emulsifiers | 0.21 |
| Methyl dioxitol | 0.48 |
| Water | 97.624 |

EXAMPLE 4

A ready to use solution; metal to azole ratio 5:1

The compositions of Examples 4 and 5 may be prepared by adding an emulsified formulation of the triazole compound to an aqueous solution of the metal ion.

| | % w/w |
|---|---|
| Copper acetate | 0.43 |
| Zinc acetate | 0.84 |
| Tebuconazole | 0.06 |
| Ester alcohol | 0.03 |
| 2-ethyl hexanoic acid | 0.03 |
| Process oil | 0.03 |
| Anionic/non-ionic emulsifier | 0.06 |
| Water | 98.52 |
| Example 5 A ready to use solution, metal to azole ratio 30:1 | |
| Copper sulphate pentahydrate | 1.18 |
| Azaconazole | 0.01 |
| Methyl dioxitol | 0.08 |
| Anionic/non-ionic emulsifiers | 0.01 |

|  | % w/w |
| --- | --- |
| Water | 98.72 |

Example 6 Two pack system

Pack A:

| | |
| --- | --- |
| Copper carbonate | 14.5 |
| Monoethanolamine | 30.7 |
| Water | 54.8 |

Pack B:

| | |
| --- | --- |
| Tebuconazole | 10 |
| Ester glycol | 50 |
| 2-ethyl hexanoic acid | 10 |
| Process oil | 10 |
| Anionic/non-ionic emulsifiers | 20 |

The ratio of copper to Tebuconazole resulting from the mixing of Pack A and Pack B can vary from 1:2.5 to 750:1 parts by weight.

The separate packs are intended to be mixed together at the treatment facility and diluted with water.

Examples 7 to 11 contain organic solvents.

|  | % w/w |
| --- | --- |
| Example 7 A concentrate | |
| Zinc versatate | 15.0 |
| Tebuconazole | 0.5 |
| Glycol ether | 10.0 |
| White spirit | 74.5 |
| Example 8 A concentrate | |
| Copper caprylate | 25.0 |
| Tebuconazole | 0.05 |
| Shellsol A | 74.75 |
| Permethrin | 0.2 |
| Example 9 A concentrate | |
| Copper acypetacs | 15.0 |
| Hexylene glycol biborate | 10.0 |
| Cypermethrin | 0.1 |
| Tebuconazole | 0.1 |
| White spirit | 74.8 |
| Example 10 A concentrate | |
| Zinc octoate | 50.0 |
| Azaconazole | 1.0 |
| Glycol ether | 49.0 |
| Example 11 A ready to use solution | |
| Copper versatate | 5.0 |
| Propiconazole | 0.01 |
| Permethrin | 0.1 |
| White spirit | 94.89 |

The compositions of Examples 12 and 13 each contain a biocidally active quaternary ammonium compound. These compounds stabilize the triazole compound in the treatment solution obtained by diluting the concentrated compositions.

Example 12 A concentrate

|  | % w/w |
| --- | --- |
| Monoethanolamine | 19.23 |
| Basic copper carbonate | 7.27 |
| Benzalkonium chloride (50% active) | 8.0 |
| Tebuconazole | 0.8 |
| Boric acid | 11.3 |

Weight ratio Cu:benzalkonium chloride:Tebuconazole 5:5:1

EXAMPLE 12(a)

A concentrate was made having the same formulation as Example 12 except that monoethanolamine was replaced by ethylenediamine.

Example 13 A concentrate

|  | % w/w |
| --- | --- |
| Monoethanolamine | 30.77 |
| Basic copper carbonate | 14.50 |
| Didecyldimethylammonium methyl sulphate (50% active) | 8.0 |
| Propiconazole | 0.32 |

Weight ratio Cu: Didecyldimethylammonium methyl sulphate: Propiconazole 2:1:0.08

EXAMPLE 13(a)

A concentrate was made having the same formulation as Example 13 except that monoethanolamine was replaced by diethanolamine.

Synergistic Action of Mixtures Formulated According to the Invention

Figure 1:
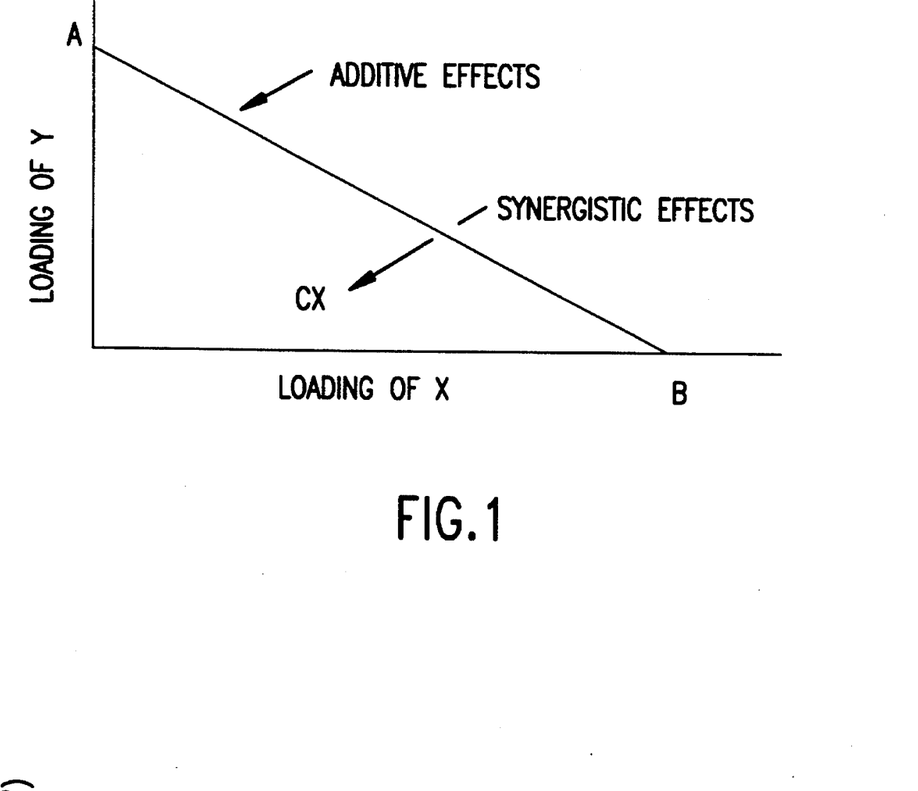
FIG. 1 is a graph correlating the additive and synergistic effects of a loading of hypothetical compound X relative to a loading of hypothetical compound Y. Points A and B are the toxic index values for biocidal compounds Y and X respectively. The straight line between the two points illustrates the toxic index values which would be obtained if the biocidal effects of compounds X and Y were merely additive.

The toxic limit value for a particular biocidal compound is the concentration of the compound which is required to prevent degradation (defined as >3% mass loss) of a substrate by a target organism. Toxic limits are normally expressed as two experimentally-determined concentrations that span the pass/fail point of the test. The toxic index is the midpoint of these two values. Where a preservative composition contains two biocidal compounds at a particular ratio, the toxic index is the estimated minimum concentration of each biocide required for effective protection of the substrate from the target organism. In FIG. 1 of the accompanying drawings, points A and B are the toxic index values for biocidal compounds Y and X respectively and the straight line between these two points illustrates the toxic index values which would be obtained if the biocidal effects of compounds X and Y are merely additive. If, for any particular ratio of X:Y, the toxic index value is found to be below the straight line (e.g. at point C), then compounds X and Y are synergistic at that particular ratio.

A convenient method of assessing the synergistic properties of a formulation is to use a 'synergistic index'. This may be defined as:

$$\text{Synergistic Index (SI)} = \frac{\text{Theoretical toxic index}}{\text{Actual toxic index}}$$

The theoretical toxic index may be calculated by interpolation to the theoretical line of action. A SI of 1 indicates no synergism. As the SI increases, so the degree of synergism also increases.

A) Compositions containing tebuconazole (i) Fungicidal effect on basidiomycete

Fungicidal activity was measured according to the test method pr EN113. This method involves treating small wood blocks with the preservative compounds and then exposing them to the decay fungi in a small test vessel. Using a range of treatment concentrations, estimation of performance is determined after a 12 week exposure period by measuring the weight loss of the blocks. Average values for weight loss for replicate samples allow the determination of an estimated concentration or loading of preservative in the wood which will be effective against the target fungus.

In order to demonstrate synergism, results have been obtained using tebuconazole alone, a substituted cuprammonium compound and then together as a mixture, the constituents of which are given as Example 1. The copper to tebuconazole ratio for this example was 25:1. All tests were carried out after cold water leaching according to the method published as EN84. Although boron was included in these formulations, this leaching procedure is sufficient to remove all of the boron. There is therefore no contribution of this active ingredient to overall efficacy in the tests. Results are given in Tables 1 and 2 for the individual active ingredients and Table 3 for the mixture.

TABLE 1

Toxic limit values for Tebuconazole as determined by EN113 (kgm$^{-3}$ active ingredient)

| | Toxic Limit kgm$^{-3}$ | Toxic Index kgm$^{-3}$ |
|---|---|---|
| P. placenta | 0.3–0.5 | 0.4 |
| C. Versicolor | 0.2–0.4 | 0.3 |
| C. puteana | 0.05–0.2 | 0.125 |

TABLE 2

Toxic limit values for substitute cuprammonium compounds determined by EN113 (kgm$^{-3}$ copper)

| | Toxic Limit kgm$^{-3}$ | Toxic Index kgm$^{-3}$ |
|---|---|---|
| P. placenta | >4.62 | Estimated value 5.0 |
| G. trabeum | >4.49 | " |
| C. puteana | 3.1–5.4 | 4.25 |

These results clearly indicate the differential performance between tebuconazole and the cuprammonium compounds. For the most aggressive fungus (Poria placenta) about 0.4 kgm$^{-3}$ Tebuconazole is required for effectiveness whilst approximately 5.0 kgm$^{-3}$ of copper is required to prevent decay.

Further results for tests using a 25:1 mixture of copper to tebuconazole are given in Table 3. Poria placenta was used as this is the most aggressive fungus in the full EN113 test towards these two compounds.

TABLE 3

Toxic limit values for a 25:1 copper:tebuconazole mixture as determined by EN113. (Toxic limit values given as kgm$^{-3}$ Cu)

| | Toxic Limit kgm$^{-3}$ Cu | Toxic Index kgm$^{-3}$ Cu |
|---|---|---|
| P. placenta | 1.4–2.2 | 1.8 |

Figure 2:
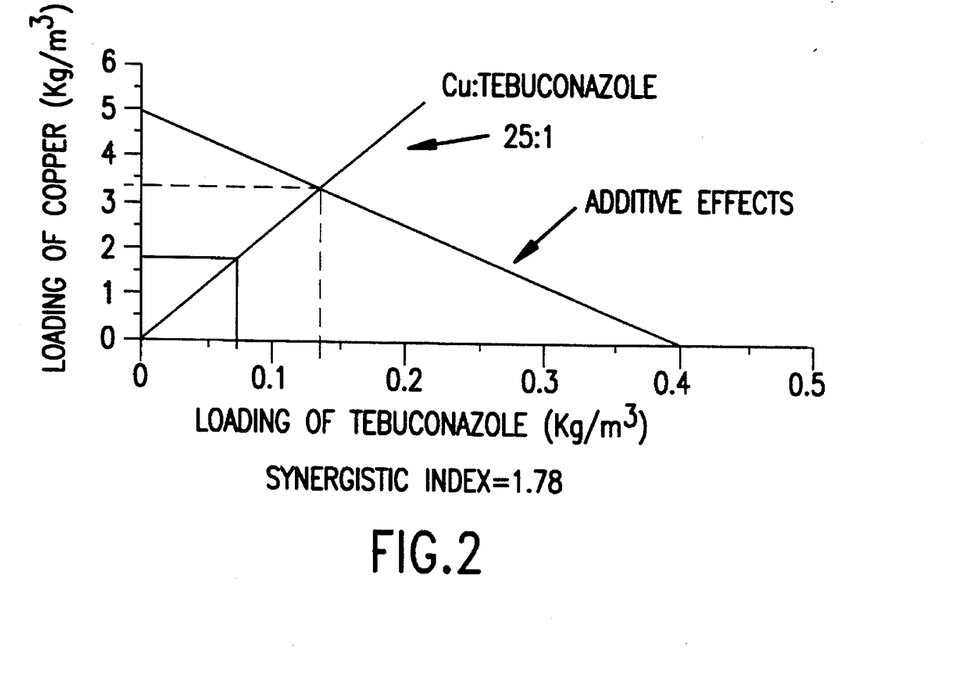
FIG. 2 is a graph correlating the loading of tebuconazole ($Kg/m^3$) and the loading of copper ($Kg/m^3$). The dotted line illustrates the expected concentration of cuprammonium compound and tebuconazole which would be needed in a composition containing copper and tebuconazole at a weight ratio of 25:1 if the performance of copper and tebuconazole were merely additive. The solid line illustrates the actual concentrations found to be required.

These results have been plotted in diagrammatic form in FIG. 2 of the accompanying drawings.

In FIG. 2, the dotted line illustrates the expected concentration of cuprammonium compound and tebuconazole which would be needed in a composition containing copper and tebuconazole at a weight ratio of 25:1 if the performance of copper and tebuconazole were merely additive (3.2 kgm$^{-3}$ copper and 0.13 kgm$^{-3}$ tebuconazole). The solid line illustrates the actual concentrations found to be required. These concentrations are considerably lower than expected (1.8 kgm$^{-3}$ copper and 0.072 kgm$^{-3}$ tebuconazole), producing a synergistic index of 1.78.

ii) Fungicidal effect of various copper:tebuconazole ratios

The above tests have been extended to delineate the range of ratios over which synergism exists between cuprammonium compounds and tebuconazole. A shortened version of the test prEN113 was used: the duration of the test was 6 weeks; the target fungus was C.puteana as the growth rate of this copper tolerant fungus is reliable in a six week exposure test. All blocks were cold-water leached according to prEN84. The compositions tested were obtained by mixing the packs A and B described in Example 6 to obtain the copper: Tebuconazole ratios shown in Table 4, which also shows the toxic and synergistic indices found at these ratios.

TABLE 4

| Formulation | Toxic Index (kgm$^{-3}$) | Theoretical Toxic Index (kgm$^{-3}$) | Synergistic Index |
|---|---|---|---|
| Tebuconazole | 0.048 ai | | |
| Cuprammonium compound | 4.91 Cu | | |
| 1:10 | 0.048 ai | 0.048 ai | 1.00 |
| 25:1 | <0.48 Cu | 0.95 Cu | >2.08 |
| 500:1 | <1.90 Cu | 4.10 Cu | >2.10 |
| 1000:1 | 4.34 Cu | 4.40 Cu | 1.01 |

N.B. Ratios given as Copper:Tebuconazole
ai - active ingredient

Figure 3:
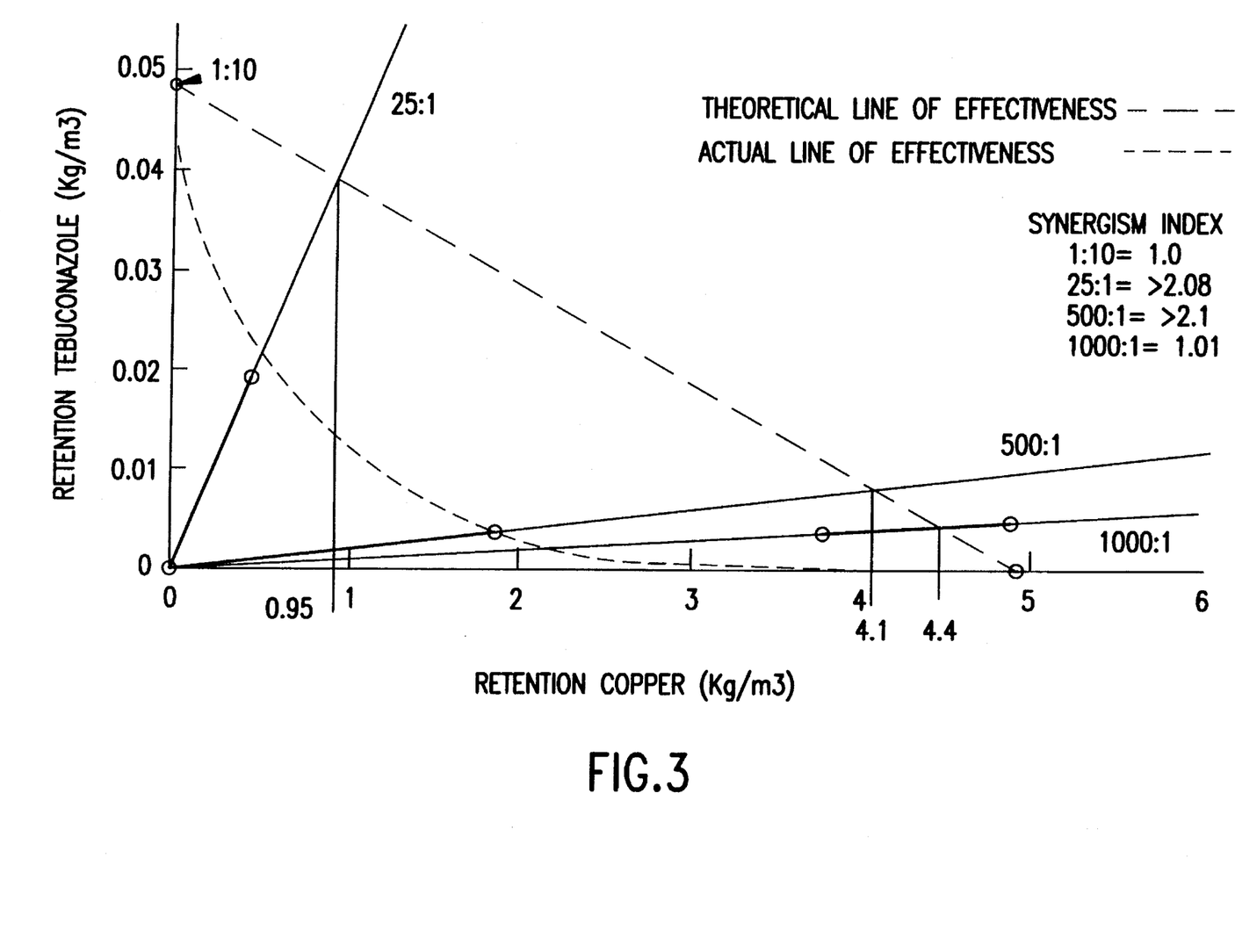
FIG. 3 is a graph correlating the retention of copper ($Kg/m^3$) and the retention of tebuconazole ($Kg/m^3$). The line with broad dashes illustrates a theoretical line of effectiveness assuming that the performance of copper and tebuconazole are merely additive. The line with narrow dashes illustrates the actual line of effectiveness. The solid lines illustrate the ratio of cuprammonium compound to tebuconazole.

These values clearly show the surprising differences in fungicidal activity exhibited by different ratios of Cu:tebuconazole; they are shown in diagrammatic form in FIG. 3. Whereas at 1:10 and 1000:1 the fungicidal activity of Cu and tebuconazole are purely additive, at 25:1 and 500:1 the formulations are significantly synergistic.

iii) Fungicidal effect against soft rot

The mixture used in the previous test was further tested in a fungal cellar test where activity against soft rot was assessed. Results from this test are particularly important in assessing the suitability of wood preservatives for use in ground contact.

Small stakes of wood (15×3×100 mm) of Beech were exposed in unsterile soil to nine-tenths of their length. The exposure period was six months. Leached samples were used. The strength loss was used as the main criteria for assessment. 80% of residual strength was used as the level at which toxic limits were determined.

Toxic thresholds on Beech against soft rot for individual components and mixtures after leaching are given below (in this table, the toxic limit and toxic index for the cuprammonium compound are given in kg of Cu per m$^3$).

TABLE 5

| | Toxic Limit (kgm$^{-3}$ active ingredient) | Toxic Index (kgm$^{-3}$ active ingredient) |
|---|---|---|
| Tebuconazole | >9.09 | >9.09 |
| Cuprammonium compound | >8.44 | >8.44 |
| Copper:Tebuconazole 25:1 | 1.65–3.25 | 2.45 |

Figure 4:
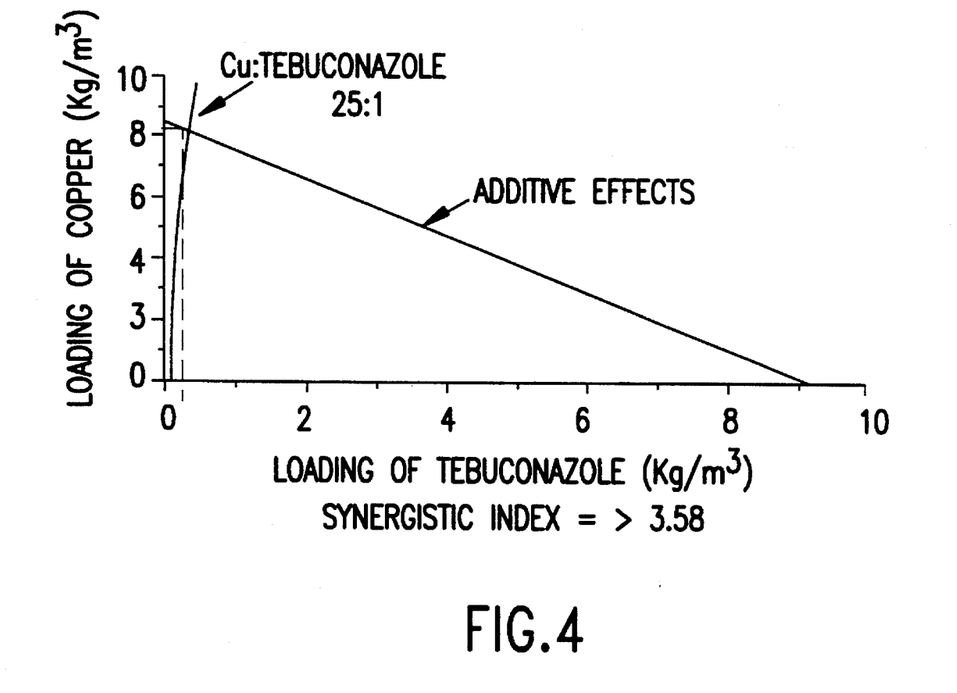
FIG. 4 is a graph correlating the loading of tebuconazole ($Kg/m^3$) and the loading of copper ($Kg/m^3$). The dotted line illustrates the expected concentrations of cuprammonium compound and tebuconazole at a weight ratio of 25:1 if the performance of copper and tebuconazole were merely additive. The solid line illustrates the actual concentrations found to be required.

The interaction between the copper and tebuconazole for performance on Beech against soft rot is shown in FIG. 4 of the accompanying drawings.

In FIG. 4, the dotted line illustrates the expected concentrations of copper and tebuconazole needed in a composition containing copper and tebuconazole at a weight ratio of 25:1 if the performance of copper and tebuconazole were merely additive (>8.44 kgm$^{-3}$ copper and >0.33 kgm$^{-3}$ tebuconazole). The solid line illustrates the actual concentrations found to be required. These concentrations are considerably lower than expected (2.44 kgm$^{-3}$ copper and 0.01 kgm$^{-3}$ tebuconazole).

These results show that the synergistic index of copper:tebuconazole combined at a ratio of 25:1 is >3.58 when tested against soft rot fungi.

B) Compositions containing either propiconazole or Azaconazole

Tests to evaluate efficacy against basidiomycetes were carried out on Propiconazole and Azaconazole singly and in mixtures with copper using ratios within the scope of the invention. The tests were carried out according to both EN113 and the method published as IRG/WP/2329, and toxic limits were identified as described above for the fungus *Coniophora puteana*.

The toxic limits are given in the table below (in this table, the toxic limit and toxic index for the duprammonium compound are given in kg of Cu per m$^3$):

TABLE 6

| Active ingredient | Toxic Limit (kgm$^{-3}$ total active ingredient) | Toxic Index (kgm$^{-3}$ total active ingredient) |
| --- | --- | --- |
| Cuprammonium compound | 3.1–5.4 | 4.25 |
| Propiconazole | 0.3–0.7 | 0.5 |
| Azaconazole | 0.7–1.3 | 1.0 |
| Cu:Propiconazole 5:1 | <0.504 | <0.504 |
| Cu:Azaconazole 5:1 | 1.008–2.04 | 1.52 |

Figure 5:
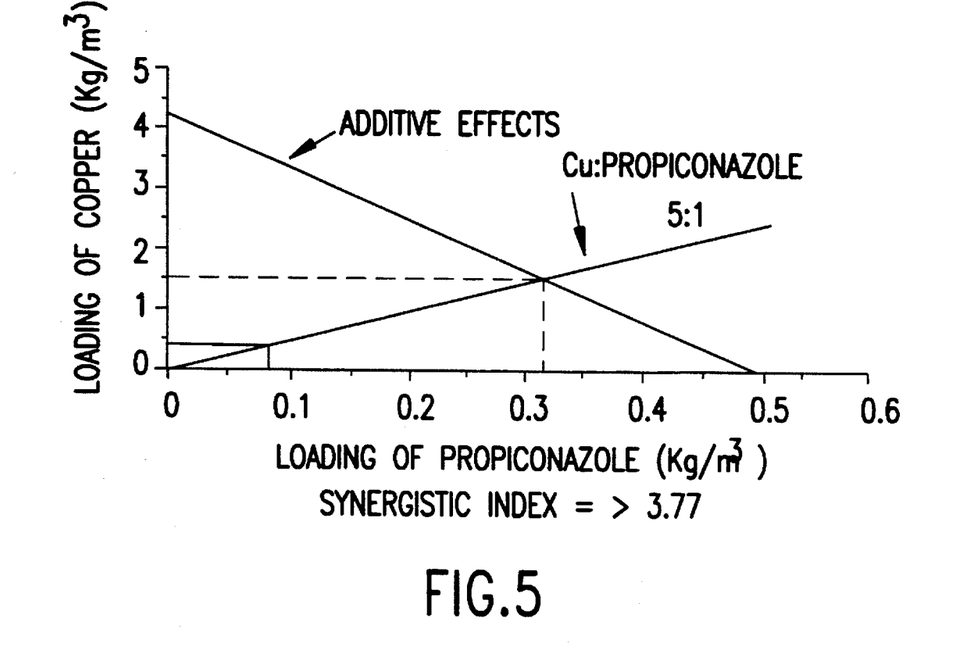
FIG. 5 is a graph correlating the loading of propiconazole ($Kg/m^3$) and the loading of copper ($Kg/m^3$). The dotted line illustrates the expected concentrations of cuprammonium compound and propiconazole at a weight ratio of 25:1 if the performance of copper and propiconazole were merely additive. The solid line illustrates the actual concentrations found to be required.
Figure 6:
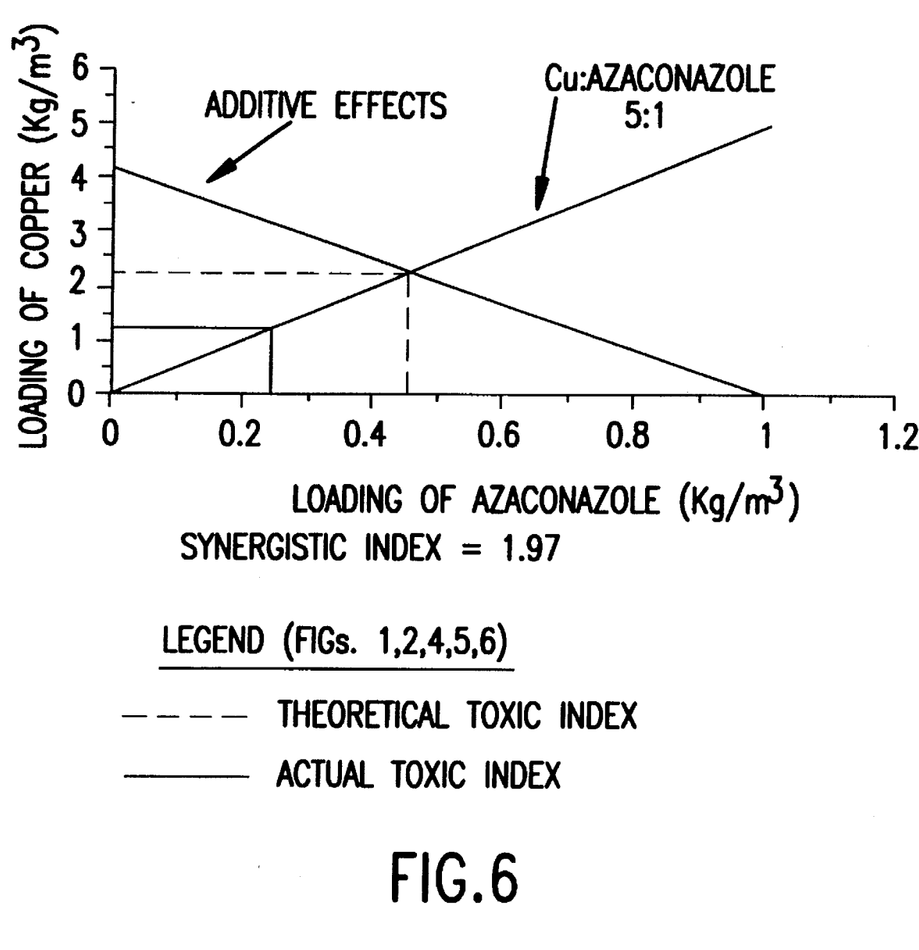
FIG. 6 is a graph correlating the loading of azaconazole ($Kg/m^3$) and the loading of copper ($Kg/m^3$). The dotted line illustrates the expected concentrations of cuprammonium compound and azaconazole at a weight ratio of 25:1 if the performance of copper and azaconazole were merely additive. The solid line illustrates the actual concentrations found to be required.

The interaction between the propiconazole and copper is illustrated in FIG. 5; and that for azaconazole and copper is illustrated in FIG. 6.

In FIG. 5, the dotted line illustrates the expected concentrations of copper and propiconazole in a composition containing copper at a weight ratio of 5:1 if the performance of copper and tebuconazole were merely additive (1.6. kgm$^{-3}$ copper and 0.3 kgm$^{-3}$ propiconazole). The solid line illustrates the actual concentrations found to be required. These concentrations are considerably lower than expected (<0.42 kgm$^{-3}$ copper and <0.084 kgm$^{-3}$ propiconazole). A synergistic of index of >3.77 was calculated from these results for Cu:Propiconazole combined at a ratio of 5:1.

In FIG. 6, the dotted line illustrates the expected concentrations of copper and azaconazole needed in a composition containing copper at a weight ratio of 5:1 if the performance of copper and azaconazole were merely additive (2.5 kgm$^{-3}$ copper and 0.5 kgm$^{-3}$ azaconazole). The solid line illustrates the actual concentrations found to be required. These concentrations are considerably lower than expected (1.26 kgm$^{-3}$ copper and 0.25 kgm$^{-3}$ azaconazole).

These results suggest that copper: azaconazole mixtures combined of a ratio of 5:1 are synergistic with a synergistic index of 1.97.

We claim:

1. A wood preservative composition comprising a synergistically effective amount of (a) a cuprammonium compound and (b) tebuconazole to preserve wood.

2. The wood preservative composition of claim 1, wherein (a) and (b) are present in a ratio of between 500:1 and 2:1 by weight.

3. The wood preservative composition of claim 1, wherein (a) and (b) are present in a ratio of between 5:1 and 50:1 by weight.

4. The wood preservative composition of claim 1, wherein (a) and (b) are present in a ratio of approximately 25:1 by weight.

5. The wood preservative composition of claim 1 wherein said cuprammonium compound is copper complexed with an alkanolamine.

* * * * *

Adverse Decisions In Interference

Patent No. 5,527,384, Gareth Williams, Judith A. Cornfield, Janet Brown, Neil P. Ryan, PRESERVATIVES FOR WOOD AND OTHER CELLULOSIC MATERIALS, Interference No. 104,078, final judgment adverse to the patentees rendered September 3, 1999, as to claims 1-5.
*(Official Gazette February 15, 2000)*